(12) United States Patent
Guenin et al.

(10) Patent No.: US 6,503,491 B2
(45) Date of Patent: *Jan. 7, 2003

(54) ELASTOMER FREE, HIGH EFFICACY ANTIPERSPIRANT STICK

(75) Inventors: Eric Guenin, Pennington, NJ (US); Jairajh Mattai, Piscataway, NJ (US); Anne Gale, Landing, NJ (US); Patricia Hall-Puzio, Succasunna, NJ (US); Wilson Lee, Bloomfield, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/035,383

(22) Filed: Nov. 9, 2001

(65) Prior Publication Data

US 2002/0081272 A1 Jun. 27, 2002

Related U.S. Application Data

(60) Provisional application No. 60/257,266, filed on Dec. 21, 2000, provisional application No. 60/257,269, filed on Dec. 21, 2000, and provisional application No. 60/257,270, filed on Dec. 21, 2000.

(51) Int. Cl.$^7$ ............................ A61K 7/32; A61K 31/74; A61K 7/00
(52) U.S. Cl. ................... 424/65; 424/78.02; 424/78.08; 424/400; 424/401; 424/DIG. 5
(58) Field of Search ................... 424/65, 78.02, 424/78.08, 400, 401, DIG. 5

(56) References Cited

U.S. PATENT DOCUMENTS

| 4,937,069 A | 6/1990 | Shin |
| 5,019,375 A | 5/1991 | Tanner et al. |
| 5,102,656 A | 4/1992 | Kasat |
| 6,375,938 B1 | 4/2002 | Clothier, Jr. et al. |

FOREIGN PATENT DOCUMENTS

| GB | 1450285 | 1/1974 |

*Primary Examiner*—Shelley A. Dodson
(74) *Attorney, Agent, or Firm*—Rosemary M. Miano

(57) ABSTRACT

A high efficacy antiperspirant/deodorant stick product may be made by combining (a) 30–70% volatile cyclomethicone; (b) 10–25% of an antiperspirant active; (c) 1–15% of an emollient; (d) 1–14% of polyethylene comprising one or more members selected from the group consisting of homopolymers and copolymers of polyethylene wherein the polyethylene (i) is at least 90% linear; (ii) has a molecular weight in the range of 300–3000 (especially 300–1000 and more especially 300–500); (iii) has a melting point in the range of 50–129 degrees C; and (iv) has a polymer backbone of $CH_3CH_2-(CH_2-CH_2)_n-H$, where n is an average number and is selected to be in the range of 10–106; (e) 0.3–7% of a wax as a co-gellant with the polyethylene wherein the wax has a melting point in the range of 40–97 degrees C.; provided that the ratio of wax:polyethylene is in the range of 1:1–1:10.

14 Claims, No Drawings

ELASTOMER FREE, HIGH EFFICACY ANTIPERSPIRANT STICK

This application is related to provisional patent applications U.S. Ser. Nos. 60/257266 and 60/257269 which were filed on the same date as the parent case for this application U.S. Ser. No. 60/257270 which was filed on Dec. 21, 2000 as a provisional case. This case is also related to two U.S. Patent applications serial numbers not yet obtained being filed on the same day as this current patent application.

FIELD OF THE INVENTION

This invention relates to antiperspirant/deodorant stick products made without stearyl alcohol and which have higher efficacy and better aesthetics than stearyl alcohol gelled sticks.

BACKGROUND OF THE INVENTION

There is a continuing trend to develop new and superior cosmetic compositions especially for the reduction and/or elimination of wetness and/or odor under the arms. Particular efforts include developing lower residue products especially with improved efficacy and aesthetics. Various product forms have included sticks (especially gel/sticks), gels, soft solids, roll-ons, aerosols and creams. Of these various forms the sticks, gels, soft solids creams and roll-ons are made with a liquid base material incorporating a solidifying agent and/or gelling agent and/or thickening agent. Generally, these forms include a solution of the cosmetically active ingredient in a suitable vehicle, a suspension of the active ingredient in a carrier vehicle, or a multiphasic dispersion or emulsion in which a solution of the active ingredient is dispersed or suspended in some continuous phase or in which the solubilized active ingredient constitutes the continuous phase.

One of the most frequently used gelling agents for stick products is stearyl alcohol. While it gives a solid product, it can reduce efficacy of the antiperspirant salt included in the formulation. This invention is a stick made without stearyl alcohol and which has an efficacy that is at least 10% better in sweat reduction than a stick that is gelled with stearyl alcohol.

Thus, it is an object of the invention to provide improved cosmetic compositions with the improvements as previously described and which are useful as antiperspirants and/or deodorants. These and other objects of the invention will be apparent from the following description of the invention.

SUMMARY OF THE INVENTION

It has been found that a high efficacy antiperspirant/deodorant stick product may be made by combining the following ingredients where all amounts are in weight percent based on the total weight of the composition:
  (a) 30–70% volatile cyclomethicone (particularly 40–50%) (for example, D4, D5, D6 and mixtures of two or more of the foregoing);
  (b) 10–25% of an antiperspirant active;
  (c) 1–15% of an emollient (which may also be a mixture of two or more emollients) and which may include a non-volatile silicone (especially wherein the emollient is selected from the group consisting of C12–15 alkyl benzoate; and medium volatility dimethicone (especially 10–350 centistoke material and more especially 10–50 centistoke material);
  (d) 1–14% of polyethylene (particularly 3–10%) comprising one or more members selected from the group consisting of homopolymers and copolymers of polyethylene wherein the polyethylene (i) is at least 90% linear; (ii) has a molecular weight in the range of 300–3000 (especially 300–1000 and more especially 300–500); (iii) has a melting point in the range of 50–129 degrees C. (for example, 50–70 degrees C., 60–70 degrees C., and 70–129 degrees C.); and (iv) has a polymer backbone of $CH_3CH_2—(CH_2—CH_2)_n—CH_2—CH_3$ (which can also be represented as $CH_3CH_2—(CH_2—CH_2)_n—H$), where n is an average number and is selected to be in the range of 10–106 (for example, polyethylenes sold under the PERFORMALENE name from New Phase Technology, Piscataway, N.J.); and
  (e) 0.3–7% of a wax (including a single was or a mixture of waxes) as a co-gellant with the polyethylene wherein the wax has a melting point in the range of 40–97 degrees C. (for example, 40–80 degrees C.), and particularly wherein the wax is a member selected from the group consisting of Japan wax substitute 525 (from Ross Wax, Jersey City, N.J.), Beeswax 136 (for example, from Ross Wax); and microcrystalline wax having a melting point in the range of 60–97 degrees C.;
provided that the ratio of wax:polyethylene is in the range of 1:1–1:10, particularly 1:2–1:10, and more particularly in a ratio of 3:8.

Other optional ingredients include 0.1–5% fragrance and an effective amount of an antimicrobial (for example, an antibacterial) agent.

DETAILED DESCRIPTION OF THE INVENTION

Various types of cyclomethicones may be used. Illustratively, and not by way of limitation, the volatile silicones are one or more members selected from the group consisting of cyclic polydimethylsiloxanes such as those represented by Formula I:

Formula I where n is an integer with a value of 3–7, particularly 5–6. By volatile silicone material is meant a material that has a measurable vapor pressure at ambient temperature. For example, DC-245 fluid or DC-345 fluid from Dow Corning Corporation (Midland, Mich.) is a type of cyclomethicone which can be used. These include a tetramer (or octylmethylcyclotetrasiloxane) and a pentamer (or decamethylcyclopentasiloxane).

The antiperspirant active can be selected from the group consisting of any of the known antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Particular types of antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.) which has 98% of the particles less than 10 microns in size.

Antiperspirant actives can be incorporated into compositions according to the present invention in amounts in the range of 10–25% (on an actives basis) of the final composition, but the amount used will depend on the formulation of the composition. At lower levels the antiperspirant active material will not substantially reduce the flow of perspiration as effectively, but will reduce malodor, for example, by acting also as an antimicrobial material.

The antiperspirant active material is desirably included as particulate matter suspended in the composition of the present invention in amounts as described above, but can also be added as solutions or added directly to the mixture.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula III:

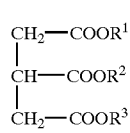

Formula III wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO-OR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^6COOH$ with the $R^6$ group having a carbon chain length between 7–10 straight chain.

(e) saturated and unsaturated fatty alcohols (including guerbet alcohols) with general structure $R^7COH$ where $R^7$ can be straight chain and have carbon length of 7 to 10.

(f) lanolin and its derivatives which are a complex esterified mixture of high molecular weight esters of (hydroxylated) fatty acids with aliphatic and alicyclic alcohols and sterols. General structures would include $R^8CH_2-(OCH_2CH_2)_nOH$ where $R^8$ represents the fatty groups derived from lanolin and n=5 to 75 or $R^9CO-(OCH_2CH_2)_nOH$ where $R^9CO-$ represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(g) alkoxylated alcohols wherein the alcohol portion is selected from aliphatic alcohols having 2–18 and more particularly 4–18 carbons, and the alkylene oxide portion is selected from the group consisting of ethylene oxide, and propylene oxide having a number of alkylene oxide units from 2–53 and, more particularly, from 2–15. Specific examples include PPG-14 butyl ether and PPG-53 butyl ether.

(h) silicones as the linear organo-substituted polysiloxanes which are polymers of silicon/oxygen with general structure:

(1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl; or (2) $HO(R^{14})_2SiO(Si(R^{15})_2O)_x Si(R^{16})_2OH$, where $R^{14}$, $R^{15}$ and $R^{16}$ can be the same or different and are each independently selected from the group consisting of phenyl and C1–C60 alkyl; (with specific examples including dimethicone, dimethiconol behenate, $C_{30-45}$ alkyl methicone, stearoxytrimethylsilane, phenyl trimethicone and stearyl dimethicone); and (i) mixtures and blends of two or more of the foregoing.

One particular group of emollients includes C12–15 alkyl benzoate (FINSOLV TN from Finetex Inc., Elmwood Park, N.J.), medium volatility dimethicone (especially 10–350 centistoke material and more especially 10–50 centistoke material), isopropyl myristate; and neopentyl glycol diheptanoate.

The emollient or emollient mixture or blend thereof incorporated in compositions according to the present invention can, illustratively, be included in amounts of 1–15%, and particularly 3–12% by weight of the total weight of the composition.

Polyethylenes may be made in a variety of ways. Each polymerization method has its own advantages and disadvantages and maybe used to obtain a polymer with specific properties. For example, free radical polymerization of ethylene using radical initiators usually gives highly branched polymers known as low-density polyethylene. This method usually requires high temperatures and pressures. Preparation of linear polyethylene can be achieved at low temperatures and pressures using transition metal compounds and organometallic compounds as a catalyst. Zeigler-Natta catalyst (for example, $TiCl_4$ and $Al(C_2H_5)_3$) is a widely used catalyst system for commercial preparation of linear polyethylene. The molecular weight of the polymer can be manipulated by controlling temperature, pressure and the ratios of the two-part catalyst system used. The molecular weight can also be controlled by using chain transfer agents such as molecular hydrogen and $Zn(C_2H_5)_2$. Active hydrogen compounds (for example, methanol) can also bring about termination of the growing chains just as they do in anionic polymerization.

The method for making both low and high molecular weight linear polyethylene is the same. Low molecular weight polymer is obtained by controlling the molecular weight using chain transfer agents such a hydrogen gas or methanol followed by isolation of the desired molecular weight through fractionation by distillation or reprecipitation with solvents of varying polarities. One can also use a catalyst system which employs a combination of transition metal compound or an element from Groups IV to VIII such as vanadium, chromium, or cobalt as well as an organometallic compound of a metal from Groups I and III of the periodic table. One typical example for making linear polyethylene is described below (see Example PE).

The polyethylenes useful in this invention include those sold under the PERFORMALENE™ product line (New Phase Technology, Piscataway, N.J.); MARCUS polyethylenes (for example M200, M300, M500 and M4040) (Marcus Oil and Chemical, Houston, Tex.; HPWax polyethylene waxes (for example, HP CWP 200, HP CWP 500 and HP 400M) (Hase Petroleum Wax Co., Arlington Heights, Ill.). Mixtures of neutral polyethylene wax/polypropylene wax may also be used such as Polarwachs® PT30, Polarwachs® PT70, and Polycerit® AT-grades (TH. C. TROMM GmbH, Germany). Suitable polyethylenes may also be made using information found in the art such as British Patent 1 450 285.

The stick antiperspirant/deodorant products of this invention is an opaque product which leaves little or no white residue when applied and which exhibits improved efficacy and stability as compared to other stick formulations made with stearyl alcohol. Reduction of sweat of at least 10% more than that achieved with sticks gelled with stearyl alcohol can be achieved with the compositions of the invention.

Suitable antimicrobial agents include, for example, bacteriostatic quaternary ammonium compounds such as 2-amino-2-methyl-1-propanol (AMP), cetyltrimethylammonium bromide, cetyl pyridinium chloride, 2,4,4'-trichloro-2'-hydroxydiphenylether (Triclosan), N-(4-chlorophenyl)-N'-(3,4-dichlorophenyl)urea (Triclocarban), silver halides, octoxyglycerin (Sensiva™ 50) and various zinc salts (for example, zinc ricinoleate). The bacteriostat can, illustratively, be included in the composition in an amount of 0–5%, particularly 0.01–1.0% by weight, of the total weight of the composition. Triclosan, can illustratively be included in an amount of from 0.05% to about 0.5% by weight, of the total weight of the composition.

A variety of fragrances can be used in these compositions if scented products are desired. Fragrances can be used in an amount in the range of 0–5%, particularly 0.01–2.0%, and, for example, at a level of 1%.

Masking agents can be used in an amount of 0.05–5.0% (particularly 0.05–2%) by weight based on the total weight of the composition if an unscented product is desired.

For additional hardening of sticks, other additives having a melting point in the range of 78–98 degrees C. such as long chain alcohols (such as Performacol 350 (having an average carbon chain length of 24 carbons), Performacol 425 (having an average carbon chain length of 30 carbons), or Performacol 550 (having an average carbon chain length of 40 carbons)); alcohol ethoxylates (such as Performathox 420 (20% by weight ethoxylation) and Performathox 450 (50% by weight ethoxylation) all available from New Phase Technology, Piscataway, N.J. may be used.

For reducing whitening in sticks liquid or solid high refractive index materials may be used such as diethylhexyl 2,6-naphthalate (from C.P. Hall Co., Chicago, Ill.) or phenyltrimethicone (from Dow Corning Corp., Midland, Mich.) as well as other suitable ingredients.

Other various optional components include those described in U.S. Pat. No. 5,019,375 to Tanner et al; U.S. Pat. No. 4,937,069 to Shin; and U.S. Pat. No. 5,102,656, each of which is incorporated by reference in its entirety herein. Examples of such additional ingredients include fragrances, coloring agents, opacificers, etc. in types and amounts conventionally used for such products.

These compositions are sticks made as suspensions and thickened or gelled by the combination of polyethylene and selected wax components.

The products of the invention can be made by conventional mixing techniques. The emollients are selected, weighed out and heated with stirring to about 65 degrees C. Next the wax component is added and heating is continued to a temperature in the range of 82–85 degrees C. The polyethylene is added. The mixture is cooled to about 80 degrees C. and the cyclomethicone (which has been preheated to about 70 degrees C.) is added. The mixture is cooled further to 75 degrees C. and the antiperspirant active is added. The temperature is increased to about 80 degrees C. and held there for about 10 minutes with mixing. Fragrance, an antibacterial agent, coloring, etc. are then added if desired and thoroughly mixed. The final mixture is poured into suitable containers and then passed through a cooling tunnel which is at about 4 degrees C. or placed in a refrigerator for a suitable length of time on a laboratory scale. Cooling is then completed (completion of cooling can also be done at room temperature).

The composition can be rubbed onto the skin from the top surface of the container (itself fed from a reservoir of product in the container) so as to deposit an adequate amount of the cosmetic composition on to the skin. The cosmetic composition, for example, an antiperspirant/deodorant may be applied to the skin in the axillary regions to deposit sufficient amounts of antiperspirant and/or deodorant active material to reduce body malodor and/or reduce perspiration in axillary regions of the human body.

Various forms of the invention can be exemplified by the following formulations but should not be construed as limitations on the invention:

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application (a) values for n, m, etc. in formulas, molecular weights and degree of ethoxylation or propoxylation are averages; (b) temperatures are in degrees C. unless otherwise indicated; and (c) the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., $7^{th}$ ed. 1997). Mixing techniques used to make the compositions are those conventionally used in the art including those described above.

Example PE

A 3-liter flask reactor is equipped with a manometer and stirring apparatus and is set at atmospheric pressure with constant stirring. The reactor temperature is set at 65 degrees C. by thermostat, purged with nitrogen, purged with ethylene, and then charged with 1 liter of purified dry cyclohexane, 4.6 millimoles of $TiCl_4$, and 2.0 millimoles of $Al(C_2H_5)_3$. Ethylene is then fed at the rate of 1 liter/minute into the reactor. After 15 minutes, the reaction is quenched by bubbling hydrogen gas through the reaction mixture. The low molecular weight polymers (which are oligomers) are separated by fractional distillation of the product mixture at reduced pressure (200 Torr, 26,664 Pascals).

Example 1
General Method of Making Compositions

The emollients (for example, dimethicone (for example, DC-200, 10 centistokes and/or DC-200 350 centistokes from Dow Corning Corp.) and C12–15 alkyl benzoate (FINSOLV TN brand product) are weighed out and placed in a 600 ml beaker. Each of the other ingredients is weighed out separately. Heating with stirring is initiated for the emollients in the 600 ml beaker until the temperature is about 65 degrees C. The wax component is then added (for example, Japan Wax Sub 525 and/or microcrystalline wax from Ross). Heating and stirring are continued until the temperature is in the range of 82–85 degrees C. The polyethylene (for example, PERFORMALENE-400 from New Phase Technology, Piscataway, N.J.) is then added with stirring. The mixture is cooled to about 80 degrees and cyclomethicone (DC-345 from Dow Corning Corp.) which has been preheated to about 70 degrees C. is then added with stirring. The mixture is further cooled to about 75 degrees C. and the antiperspirant active salt (for example, Reach AZZ 902 SUF aluminum zirconium salt or Reach AZP 908 from Reheis Inc., Berkeley Heights, N.J.) is added with mixing. The temperature is increased to about 80 degrees C. and held there for about 10 minutes with mixing. Fragrance is added and mixing is continued for 1 minute. The mixture is poured into oval containers of the type normally used for antiperspirant/deodorant products and placed in a refrigerator at about 4 degrees C. for about 15 minutes. Cooling is completed at room temperature.

In some of the examples additional ingredients such as diethylhexyl 2,6-naphthalate or Performacol 350 alcohol can be added.

We claim:

1. A high efficacy stick antiperspirant/deodorant free of added stearyl alcohol and comprising in weight percent based on the total weight of the composition:
   (a) 30–70% volatile cyclomethicone;
   (b) 10–25% of an antiperspirant active;
   (c) 1–15% of an emollient;
   (d) 1–14% of polyethylene comprising one or more members selected from the group consisting of homopolymers and copolymers of polyethylene wherein the polyethylene (i) is at least 90% linear; (ii) has a molecular weight in the range of 300–3000; (iii) has a melting point in the range of 50–129 degrees C.; and (iv) has a polymer backbone of $CH_3CH_2$—$(CH_2$—$CH_2)_n$—$CH_2$—$CH_3$, where n is an average number and is selected to be in the range of 10–106; and
   (e) 0.3–7% of a wax as a co-gellant with the polyethylene wherein the wax has a melting point in the range of 40–97 degrees C.; provided that the ratio of wax:polyethylene is in the range of 1:1–1:10.

2. A stick as claimed in claim 1 comprising 40–50% of a volatile silicone.

3. A stick as claimed in claim 1 wherein the emollient comprises a mixture of two or more emollients.

4. A stick as claimed in claim 1 comprising 3–12% emollient.

5. A stick as claimed in claim 1 wherein the emollient comprises a non-volatile silicone.

6. A stick as claimed in claim 5 wherein the emollient comprises a 10–350 centistoke dimethicone.

7. A stick as claimed in claim 1 wherein the emollient is a member of the group consisting of
   (a) fats and oils represented by Formula III:

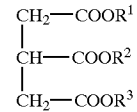

Formula III wherein each of $R^1$, $R^2$, and $R^3$ may be the same or different and have a carbon chain length (saturated or unsaturated) of 7 to 30;
   (b) hydrocarbons selected from the group consisting of paraffin, petrolatum, hydrogenated polyisobutene, and mineral oil;
   (c) esters of general structure would be $R^4CO$—$OR^5$ wherein the chain length for $R^4$ and $R^5$ hydrocarbon groups is in the range of 7–30 and can be saturated or unsaturated, straight chained or branched;
   (d) saturated and unsaturated fatty acids which have general structure $R^6COOH$ with the $R^6$ group being a straight chain hydrocarbon with a carbon chain length between 7–10;

(e) saturated and unsaturated fatty alcohols which have a general structure $R^7COH$ where $R^7$ is a straight chain hydrocarbon with a carbon length of 7 to 10;

(f) lanolin and its derivatives selected from the group consisting of lanolin, lanolin oil, lanolin wax, lanolin alcohols, lanolin fatty acids, isopropyl lanolate, ethoxylated lanolin and acetylated lanolin alcohols;

(g) alkoxylated alcohols wherein the alcohol portion is selected from aliphatic alcohols having 2–18 carbons, and the alkylene oxide portion is selected from the group consisting of ethylene oxide, and propylene oxide having a number of alkylene oxide units from 2–53;

(h) silicones as the linear organo-substituted polysiloxanes which are polymers of silicon/oxygen with general structure:

(1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl; or (2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl; and (i) mixtures and blends of two or more of the foregoing.

8. A stick as claimed in claim 1 comprising 3–10% polyethylene.

9. A stick as claimed in claim 1 wherein the polyethylene has a melting point in the range of 50–70 degrees C.

10. A stick as claimed in claim 1 wherein the polyethylene has a melting point in the range of 60–70 degrees C.

11. A stick as claimed in claim 1 wherein the polyethylene has a melting point in the range of 70–129 C.

12. A stick as claimed in claim 1 wherein the wax has a melting point in the range of 40–80 degrees C.

13. A stick as claimed in claim 1 wherein the wax is a microcrystalline wax having a melting point in the range of 60–97 degrees C.

14. A stick as claimed in claim 1 additionally comprising an effective amount of an antimicrobial agent.

* * * * *

(12) EX PARTE REEXAMINATION CERTIFICATE (5486th)
United States Patent
Guenin et al.

(10) Number: US 6,503,491 C1
(45) Certificate Issued: Aug. 29, 2006

(54) ELASTOMER FREE, HIGH EFFICACY ANTIPERSPIRANT STICK

(75) Inventors: Eric Guenin, Pennington, NJ (US); Jairajh Mattai, Piscataway, NJ (US); Anne Gale, Landing, NJ (US); Patricia Hall-Puzio, Succasunna, NJ (US); Wilson Lee, Bloomfield, NJ (US)

(73) Assignee: Colgate-Palmolive Company, New York, NY (US)

Reexamination Request:
No. 90/006,628, May 6, 2003
No. 90/007,071, Jun. 9, 2004

Reexamination Certificate for:
Patent No.: 6,503,491
Issued: Jan. 7, 2003
Appl. No.: 10/035,383
Filed: Nov. 9, 2001

Related U.S. Application Data

(60) Provisional application No. 60/257,266, filed on Dec. 21, 2000, provisional application No. 60/257,269, filed on Dec. 21, 2000, and provisional application No. 60/257,270, filed on Dec. 21, 2000.

(51) Int. Cl.
*A61K 7/32* (2006.01)
*A61K 31/74* (2006.01)
*A61K 7/00* (2006.01)

(52) U.S. Cl. ............... 424/65; 424/78.02; 424/78.08; 424/400; 424/401; 424/DIG. 5

(58) Field of Classification Search ............... 424/400, 424/401, 65, 66, 67, 68, 78.02, 78.08, DIG. 5
See application file for complete search history.

(56) References Cited

U.S. PATENT DOCUMENTS

| | | | | |
|---|---|---|---|---|
| 5,417,964 A | * | 5/1995 | Carlson et al. | 424/66 |
| 6,171,581 B1 | * | 1/2001 | Joshi et al. | 424/65 |
| 6,177,066 B1 | * | 1/2001 | Pataut et al. | 424/65 |

FOREIGN PATENT DOCUMENTS

EP 953335 B1 * 1/2002

* cited by examiner

*Primary Examiner*—Gary Kunz

(57) ABSTRACT

A high efficacy antiperspirant/deodorant stick product may be made by combining (a) 30–70% volatile cyclomethicone; (b) 10–25% of an antiperspirant active; (c) 1–15% of an emollient; (d) 1–14% of polyethylene comprising one or more members selected from the group consisting of homopolymers and copolymers of polyethylene wherein the polyethylene (i) is at least 90% linear; (ii) has a molecular weight in the range of 300–3000 (especially 300–1000 and more especially 300–500); (iii) has a melting point in the range of 50–129 degrees C; and (iv) has a polymer backbone of $CH_3CH_2\text{---}(CH_2\text{---}CH_2)_n\text{---}H$, where n is an average number and is selected to be in the range of 10–106; (e) 0.3–7% of a wax as a co-gellant with the polyethylene wherein the wax has a melting point in the range of 40–97 degrees C.; provided that the ratio of wax:polyethylene is in the range of 1:1–1:10.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claim 1 is determined to be patentable as amended.

Claims 3–14, dependent on an amended claim, are determined to be patentable.

New claim 15 is added and determined to be patentable.

1. A highly efficacy stick antiperspirant/deodorant free of added stearyl alcohol and comprising in weight percent based on the total weight of the composition:
   (a) [30–70%] *40–50%* volatile cyclomethicone;
   (b) 10–25% of an antiperspirant active;
   (c) 1–15% of an emollient;
   (d) 1–14% of polyethylene comprising one or more members selected from the group consisting of homopolymers and copolymers of polyethylene wherein the polyethylene (i) is at least 90% linear; (ii) has a molecular weight in the range of 300–3000; (iii) has a melting point in the range of 50–129 degrees C.; and (iv) has a polymer backbone of $CH_3CH_2-(CH_2-CH_2)_n-CH_2-CH_3$, where n is an average number and is selected to be in the range of 10–106; and
   (e) 0.3–7% of a wax as a co-gellant with the polyethylene wherein the wax has a melting point in the range of 40–97 degrees C.; provided that the ratio of wax:polyethylene is in the range of 1:1–1:10.

*15. The stick as claimed in claim 1, wherein the stick is elastometer free.*

\* \* \* \* \*